United States Patent [19]

Biollaz

[11] Patent Number: 5,378,710
[45] Date of Patent: * Jan. 3, 1995

[54] 17β-SUBSTITUTED AZA-ANDROSTANE DERIVATIVES

[75] Inventor: Michel Biollaz, Binningen, Switzerland

[73] Assignee: Ciba-Geigy Corp., Ardsley, N.Y.

[*] Notice: The portion of the term of this patent subsequent to Apr. 19, 2011 has been disclaimed.

[21] Appl. No.: 132,399

[22] Filed: Oct. 6, 1993

Related U.S. Application Data

[63] Continuation of Ser. No. 954,081, Sep. 30, 1992, Pat. No. 5,304,562.

[30] Foreign Application Priority Data

Oct. 9, 1991 [CH] Switzerland ............................ 2978

[51] Int. Cl.$^6$ ............................................ C07D 221/02
[52] U.S. Cl. ........................................ 514/284; 546/77
[58] Field of Search ............................ 514/284; 546/77

[56] References Cited

U.S. PATENT DOCUMENTS

| | | | |
|---|---|---|---|
| 4,377,584 | 3/1983 | Rasmusson et al. | 546/77 |
| 4,760,071 | 7/1988 | Rasmussen | 546/77 |
| 5,120,847 | 6/1992 | King et al. | 546/77 |
| 5,302,621 | 4/1994 | Kojima | 514/284 |
| 5,304,562 | 4/1994 | Biollaz | 546/77 |

FOREIGN PATENT DOCUMENTS

| | | | |
|---|---|---|---|
| 155096 | 3/1985 | European Pat. Off. | |
| 0200859 | 11/1986 | European Pat. Off. | |
| 271219 | 6/1988 | European Pat. Off. | 546/77 |
| 271220 | 6/1988 | European Pat. Off. | 546/77 |
| 277002 | 8/1988 | European Pat. Off. | 546/77 |
| 285383 | 10/1988 | European Pat. Off. | |
| 367502 | 5/1990 | European Pat. Off. | 546/77 |
| 0414490 | 2/1991 | European Pat. Off. | 546/77 |
| 0414491 | 2/1991 | European Pat. Off. | 546/77 |
| 0484094 | 5/1992 | European Pat. Off. | |
| 9100732 | 1/1991 | WIPO | |

OTHER PUBLICATIONS

Stinson, Chem and Eng News, 24 Jun. 1992 pp. 7-8 (1992).
Rasmusson et al., Azasteroids As Inhibitors Of Rat Prostatic 5α-Reductase. J. Med Chem. 1984, 1690-1701.
Bhattacharya et al., Silylation-Mediated Oxidation of 4-Aza-3-Ketosteroids with DDQ Proceeds via DDQ--substrate Adducts J. Am. Chem. Soc. 1988 110, 3318-19.
Rasmusson et al., J. Med. Chem 1986, 29, 2298-2315, Azasteroids: Structure Activity Relationships For Inhibition of 5α-Reductase And Of Androgen Receptor Binding.

Primary Examiner—Donald G. Daus
Attorney, Agent, or Firm—Irving M. Fishman; Karen G. Kaiser

[57] ABSTRACT

Compounds of the formula

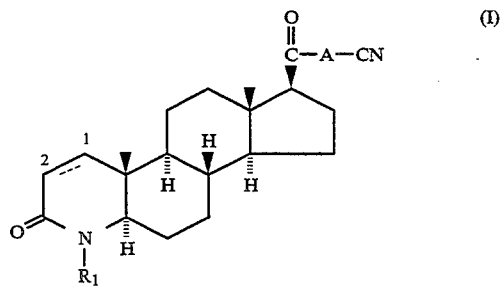

wherein carbon atoms 1 and 2 are linked by a single bond or a double bond, $R_1$ is hydrogen, methyl or ethyl, and A is a group of the formula —N(—$R_2$)—X— wherein $R_2$ is hydrogen or $C_1$–$C_4$alkyl and X is $C_1$–$C_{12}$alkylene or $C_3$–$C_6$cycloalkylidene; a group of the formula —N(—$R_2$)—Y—Phe— wherein $R_2$ is as defined above, Y is a direct bond or $C_1$–$C_6$-alkylene and Phe is an unsubstituted or substituted phenylene radical; a group of the formula —O—X— wherein X is as defined above, or a group —O—Y—Phe— wherein Y and Phe are as defined above, are inhibitors of 5α-reductase and can be used for the therapeutic treatment of the human and animal body.

6 Claims, No Drawings

17β-SUBSTITUTED AZA-ANDROSTANE DERIVATIVES

This application is a continuation of Ser. No. 07/954,081, filed Sep. 30, 1992, now U.S. Pat. No. 5,304,562.

The invention relates to novel 17β-substituted aza-androstane derivatives of the formula

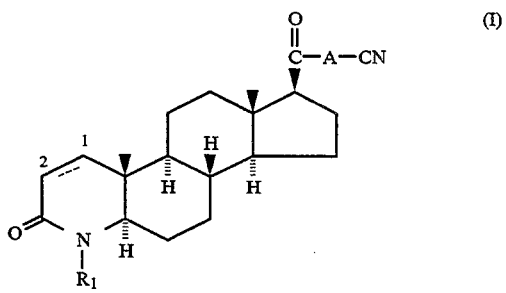

wherein carbon atoms 1 and 2 are linked by a single bond or a double bond, $R_1$ is hydrogen, methyl or ethyl, and A is a group of the formula —N(—$R_2$)—X— wherein $R_2$ is hydrogen or $C_1$–$C_4$alkyl and X is $C_1$–$C_{12}$alkylene or $C_3$–$C_6$cycloalkylidene; a group of the formula —N(—$R_2$)—Y—Phe— wherein $R_2$ is as defined above, Y is a direct bond or $C_1$–$C_6$alkylene and Phe is an unsubstituted or substituted phenylene radical; a group of the formula —O—X— wherein X is as defined above, or a group —O—Y—Phe— wherein Y and Phe are as defined above.

The invention relates also to processes for the preparation of the above-mentioned compounds, and to pharmaceutical compositions comprising those compounds and to processes for the preparation thereof; the invention relates also to the therapeutic use of those compounds and of pharmaceutical compositions comprising them in warm-blooded animals, including humans.

The definitions used hereinbefore and hereinafter preferably have the following meanings in the context of this description:

$C_1$–$C_4$alkyl is corresponding straight-chain or branched alkyl and is, for example, n-propyl, n-butyl, isopropyl, tert-butyl and especially methyl and ethyl.

$C_1$–$C_{12}$alkylene as a radical X may be linear or branched as desired, the two free valencies originating from two different carbon atoms or from the same carbon atom. Preference is given both to linear $C_2$–$C_6$alkylene radicals, for example tri- to hexa-methylene, especially pentamethylene, and ethylene, and to branched $C_3$–$C_6$alkylene radicals, for example 2-methyl-1,2-propylene and 1,1-dimethylethylene, that have the free valencies at two different carbon atoms. Special emphasis is given also to linear or at most singly branched alkylene radicals of which the two free valencies originate from the same carbon atom, for example linear or singly branched $C_1$–$C_6$alkylidene radicals, such as, especially, methylene, but also ethylidene, 1,1-propylidene or 2,2-propylidene. In accordance with the above definition oft he term "alkylene" it is possible, for example, for 1,1-alkylidene radicals also to be designated 1,1-alkylene radicals.

$C_3$–$C_6$cycloalkylidene is 1,1-cyclopropylidene, 1,1-cyclobutylidene, 1,1-cyclopentylidene and 1,1-cyclohexylidene.

$C_1$–$C_6$alkylene (Y) may be linear or branched. Linear $C_1$–$C_4$alkylene, for example methylene, ethylene, trimethylene and tetramethylene, is preferred.

Phenylene is ortho (o—), meta (m—) and especially para (p—) phenylene and may—apart from the cyano group—be unsubstituted or may carry one, two or three further substituents selected from the group halogen, $C_1$–$C_4$alkyl, $C_1$–$C_4$alkoxy, hydroxy, nitro, cyano and $C_1$–$C_4$alkoxycarbonyl.

Halogen is, for example, fluorine or chlorine.

$C_1$–$C_4$alkoxy is, for example, propoxy, butoxy and especially methoxy and ethoxy.

$C_1$–$C_4$alkoxycarbonyl is, for example, propoxycarbonyl, tert-butoxycarbonyl and especially methoxycarbonyl and ethoxycarbonyl.

The compounds of formula I exhibit valuable pharmacological properties. In particular, they are potent inhibitors of the enzyme 5α-reductase which is responsible for the conversion of the androgen testosterone, which circulates predominantly in men, into the even more strongly active 5α-dihydrotestosterone. In benign hypertrophy of the prostate, 5α-dihydrotestosterone is detected in increased concentrations in the prostate and is therefore held responsible for the hypertrophy. It has now been found that the compounds of formula I according to the invention exert a strong inhibitory action on the enzyme 5α-reductase.

The compounds of formula I according to the invention are therefore suitable in warm-blooded animals (humans and animals) for the therapeutic treatment of benign hypertrophy of the prostate and other disorders and conditions that respond favourably to a reduction in the mount of physiological 5α-dihydrotestosterone, such as carcinoma of the prostate, seborrhoea, Acne vulgaris, hirsutism in women and the like. The novel compounds may be used as enterally, for example orally, topically or parenterally administrable 5α-reductase inhibitors, for example in the form of suitable pharmaceutical compositions.

The invention relates especially to compounds of formula I wherein carbon atoms 1 and 2 are linked by a single bond or a double bond, $R_1$ is hydrogen, methyl or ethyl, and A is a group of the formula —N(—$R_2$)—X— wherein $R_2$ is hydrogen or $C_1$–$C_4$alkyl, especially methyl, and X is straight-chain or branched $C_1$–$C_{12}$alkylene, especially $C_1$–$C_6$alkylene, such as ethylene, pentamethylene, 2-methyl-1,2-propylene or 2,2-propylidene, or $C_3$–$C_6$cycloalkylidene, for example 1,1-cyclopropylidene; a group of the formula —N(—$R_2$)—Y—Phe— wherein $R_2$ is as defined above, Y is a direct bond or $C_1$–$C_6$alkylene, especially $C_1$–$C_4$alkylene, for example methylene, and Phe is a phenylene radical that is unsubstituted or substituted by halogen, for example chlorine, $C_1$–$C_4$alkyl, for example methyl, $C_1$–$C_4$–alkoxy, such as methoxy, hydroxy, nitro, cyano and/or by $C_1$–$C_4$alkoxycarbonyl, for example methoxycarbonyl; a group of the formula —O—X— wherein X is as defined above, or a group —O—Y—Phe wherein Y and Phe are as defined above.

The invention relates more especially to compounds of formula I wherein carbon atoms 1 and 2 are linked by a single bond or a double bond, $R_1$ is hydrogen or methyl, and A is a group of the formula —N(—$R_2$)—X— wherein $R_2$ is hydrogen and X is straight-chain or branched $C_1$–$C_6$alkylene, especially ethylene, pentamethylene, 2-methyl-1,2-propylene or 2,2-propylidene; a group of the formula —N(—$R_2$)—Y—Phe— wherein $R_2$ is as defined above, Y is a direct bond or $C_1$–$C_4$alkylene, for example methylene, and Phe is a phenylene radical that is unsubstituted or substituted by halogen, for example chlorine, $C_1-C_4$alkyl, for example methyl, $C_1-C_4$alkoxy, such as methoxy, hydroxy, nitro, cyano or by $C_1-C_4$alkoxycarbonyl, for example methoxycarbonyl; a group of the formula —O—X— wherein X is as defined above, or a group —O—Y—Phe— wherein Y and Phe are as defined above.

Special mention should be made of compounds of formula I wherein carbon atoms 1 and 2 are linked by a double bond, $R_1$ is hydrogen, and A is a group of the formula —N(—$R_2$)—X— wherein $R_2$ is hydrogen and X is $C_1-C_4$alkylene, especially 2,2-propylidene; or a group of the formula —N(—$R_2$)—Y—Phe— wherein $R_2$ is as defined above, Y is a direct bond and Phe is a p-phenylene radical.

The invention relates preferably to the compounds of formula I described in the Examples.

The compounds of the present invention are obtained by processes known per se.

The compounds of formula I according to the invention are prepared, for example, by (a) reacting a compound of formula

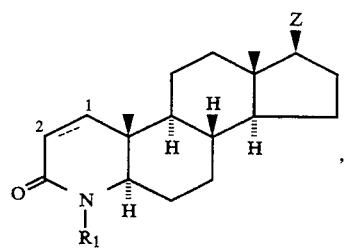

(II)

wherein carbon atoms 1 and 2 are linked by a single bond or a double bond, $R_1$ is as defined for formula I, and Z is carboxy or a reactively activated carboxy group, with a compound of the formula H—$A_1$—CN wherein $A_1$ is a group of the formula —N(—$R_2$)—X— or a group of the formula —N(—$R_2$)—Y—Phe—, or with a compound of the formula H—$A_2$—CN wherein $A_2$ is a group of the formula —O—X— or a group of the formula —O—Y—Phe—, wherein $R_2$, X, Y and Phe are as defined for formula I, or (b) in a compound of formula

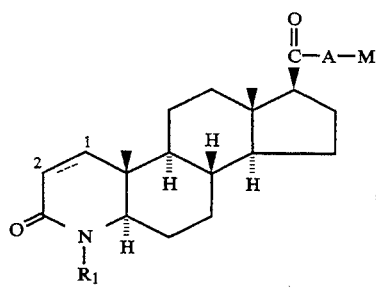

(III)

wherein carbon atoms 1 and 2 are linked by a single bond or a double bond, $R_1$ and A are as defined for formula I, and M is a radical that can be convened into cyano, convening the radical M into cyano, or (c) for the preparation of a compound of formula I wherein carbon atoms 1 and 2 are linked by a single bond, and $R_1$ and A are as deemed above, treating a compound of formula

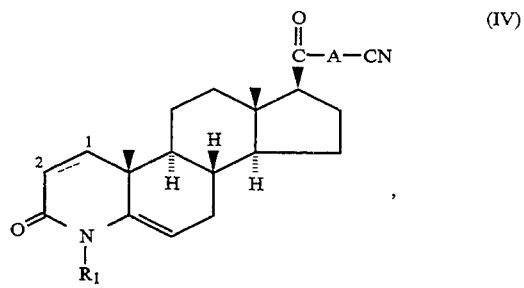

(IV)

with a reducing agent, and, if desired, convening a compound of formula I obtainable in accordance with the process into a different compound of formula I.

Process (a) is an acylation reaction. An amino compound of the formula H—$A_1$—CN or a hydroxy compound of the formula H—$A_2$—CN is acylated with a carboxylic acid or a reactive derivative thereof to form an acid amide (carboxamide) or an ester (carboxylate), respectively, it also being possible for the activation of the carboxylic acid used as acylating agent to be effected in the presence of the compound to be acylated (see, for example, Haslam, E., Tetrahedron 36, 2409–2433 (1980)).

Carboxylic acid derivatives that can be used as acylating agents are especially reactive activated esters or reactive anhydrides, and also reactive cyclic amides.

Suitable activated esters are, for example, esters of the amidino type, such as N,N'-disubstituted amidino esters, which can be obtained, for example, by treatment of the corresponding acid of formula II wherein Z is carboxy with a suitable N,N'-disubstituted carbodiimide, for example N,N'-dicyclohexylcarbodiimide (carbodiimide method); thioesters, especially 2-pyridylthio esters, which are formed, for example, by reaction of the corresponding acid with triphenylphosphine and 2,2'-dithio-dipyridine (activated thio esters method); or N-hydroxy esters, for example amino esters or amido esters, which can be obtained, for example, by treatment of the corresponding acid with an N-hydroxyamino or N-hydroxyamido compound, respectively, for example N-hydroxysuccinimide, N-hydroxypiperidine, N-hydroxyphthalimide or 1-hydroxybenzotriazole, for example in accordance with the carbodiimide method- The preferred amino esters include benzotriazol-1-yloxy derivatives. The latter are formed, for example, by reaction of the corresponding acid of formula II wherein Z is carboxy with a suitable benzotriazole derivative, especially benzotriazol-1-yloxy-tris(-dimethylamino)phosphonium hexafluorophosphate (Castros reagent) or O—(1H-benzotriazol-1-yl)—N,N,N',N'-tetramethyluronium hexafluorophosphate.

Suitable acid anhydrides are especially mixed anhydrides of an acid of formula II wherein Z is carboxy, therefore, for example, anhydrides with inorganic acids, such as acid halides, especially acid chlorides, which are obtained, for example, by treatment of the corresponding acid with oxalyl chloride, thionyl chloride or 1-chloro-1-dimethylamino-2-methyl-prop-1-ene (acid chloride method).

Suitable cyclic amides are especially amides with five-membered diazacycles of aromatic character, such as amides with imidazoles, for example imidazole, which can be obtained, for example, by treatment of the corresponding acid with N,N'-carbonyldiimidazole (imidazolide method).

As mentioned above, derivatives of acids that can be used as acylating agents can be formed in situ. For example, N-hydroxy esters can be formed in situ by reacting a mixture of the starting material to be acylated and the acid used as acylating agent in the presence of a suitable benzotriazole derivative, for example benzotriazol-1-yloxy-tris(dimethylamino)phosphonium hexafluorophosphate. Furthermore, amino or amido esters of the acids used as acylating agent can be formed in situ in the presence of the starting material to be acylated by reacting a mixture of the corresponding acid and amino starting materials in the presence of an N,N'-disubstituted carbodiimide, for example N,N'-dicyclohexylcarbodiimide, and an N-hydroxyamine, especially hydroxybenzotriazole, or an N-hydroxyamide, for example N-hydroxysuccinimide, optionally in the presence of a suitable base, for example 4-dimethylaminopyridine. N,N'-disubstituted amidino esters are formed, for example, in situ by the reaction of the compound to be acylated with the acid used as acylating agent in the presence of a suitable N,N-disubstituted carbodiimide, for example N,N'-dicyclohexylcarbodiimide.

The acylation can be carried out in a manner known per se, usually at temperatures between the freezing point and the boiling point of the reaction mixture, such as in a temperature range of from approximately $-10°$ to approximately $+150°$ C., preferably from room temperature (about $+20°$ C.) to approximately $+70°$ C., for example in a closed reaction vessel and/or in the atmosphere of an inert gas, for example nitrogen, in the presence of a suitable solvent, preferably an inert solvent, such as dimethylformamide (DMF), an ether, for example tetrahydrofuran (THF), or a halogenated, especially chlorinated, aliphatic hydrocarbon, for example chloroform or methylene chloride, and optionally in the presence of an acid-binding agent, for example a base. A suitable base is, for example, an amine, for example a tertiary amine, such as a tri($C_1$-$C_4$)alkylamine, such as trimethylamine, triethylamine or ethyldiisopropylamine, or an arylalkylamine, for example N,N-dimethylaniline, or a cyclic tertiary amine, for example N-$C_1$-$C_4$alkylmorpholine, for example N-methylmorpholine, or a base of the pyridine type, for example pyridine or quinoline.

Process (b) is carried out in accordance with known methods for the introduction of the cyano group.

Radicals M in a compound of formula HI that can be converted into cyano are, for example, hydrogen; esterified hydroxy groups, for example halogen, especially chlorine, bromine or iodine, or sulfonyloxy, for example toluenesulfonyloxy, benzenesulfonyloxy or methanesulfonyloxy; carboxy, carboxy in the form of a functional derivative, for example aminocarbonyl, $C_1$-$C_4$alkylaminocarbonyl, for example tert-butylaminocarbonyl, or formyl in the form of a functional derivative, for example hydroxyiminomethyl.

Compounds of formula I can be obtained in accordance with process (b), for example, by the following reactions:

The reaction of a compound of formula III wherein M is halogen, for example chlorine, bromine or iodine, to form a corresponding compound of formula I is carried out, for example, using a cyanide salt, especially sodium or potassium cyanide or copper(I) cyanide. High temperatures are preferred, especially the reflux temperature of the reaction mixture.

The reaction of a compound of formula III wherein M is sulfonyloxy, for example p-toluenesulfonyloxy, benzenesulfonyloxy or methanesulfonyloxy, to form a corresponding compound of formula I is carried out, for example, by reaction with an alkali metal cyanide, preferably sodium or potassium cyanide. High temperatures arc preferred, especially the reflux temperature of the reaction mixture.

The conversion of a compound of formula HI wherein M is carboxy into a compound of formula I can be carried out, for example, by reaction with a chlorosulfonyl isocyanate in, for example, dimethylformamide (DMF) in accordance with the method of R. Graf in Angew. Chem. 80, 183 (1968).

The conversion of a compound of formula III wherein M is carboxy in the form of a functional derivative, for example in the form of aminocarbonyl or $C_1$-$C_4$alkylaminocarbonyl, advantageously in the form of tert-butylaminocarbonyl, into a compound of formula I can be carried out, for example, using a strong dehydrating agent, for example phosphorus(V) oxide, phosphoryl chloride, thionyl chloride, tosyl chloride, mesyl chloride or oxalyl chloride. The dehydration is preferably effected in an inert anhydrous solvent, for example an ether, for example tetrahydrofuran or dioxane, DMF, and also pyridine, at room temperature or slightly reduced or elevated temperature, for example at from approximately 0° C. to approximately 80° C.

The conversion of a compound of formula HI wherein M is formyl into a corresponding compound of formula I is cameo out, for example, after conversion of the formyl group into a functional derivative, for example hydroxyiminomethyl (aldoxime), and conversion of that group into a cyano group by means of a dehydrating agent. The conversion of the formyl group into the hydroxyiminomethyl group is effected, for example, by reaction with a salt of hydroxylamine, preferably the hydrochloride. A suitable dehydrating agent is, for example, one of those mentioned above, for example phosphorus(V) oxide or thionyl chloride, the anhydride of an organic acid, for example the anhydride of a $C_1$-$C_4$-alkanoic acid, preferably acetic anhydride, oxalic acid diimidazolide (see T. Kitagawa et al., Chem. Pharm. Bull. 33, 4014 (1985)) or benzeneselenyl chloride (see G. Sosnovsky, J. A. Rogh, Z. Naturforsch. Vol. 34, 511 (1979)). The dehydration is carried out in a manner known per se, for example in the presence of a suitable solvent, preferably an inert anhydrous solvent, such as an ether, for example diethyl ether or tetrahydrofuran (THF), a halogenated, especially chlorinated, aliphatic hydrocarbon, for example chloroform or methylene chloride, or an aromatic hydrocarbon, for example benzene.

A compound of formula III wherein M is formyl can also be converted directly into the corresponding nitrile of formula I, for example by reaction with O,N-bis(trifluoroacetyl)hydroxylamine in the presence of a base, for example pyridine, in accordance with the method of D. T. Mowry, Chem. Revs. 42, 251 (1948).

Compounds of formula I can be obtained in accordance with process (c) by reduction of a compound of formula IV, especially reduction with hydrogen in the presence of a transition metal catalyst (catalytic hydrogenation). The catalytic hydrogenation is carried out, for example, with palladium or with platinum oxide, optionally with the addition of carbon, preferably in an acidic medium, for example glacial acetic acid.

Compounds of formula I obtainable in accordance with the process can be convened in a manner known per se into different compounds of formula I.

For example, compounds of formula I wherein $R_1$ and/or $R_2$ are hydrogen can be converted by reaction with a strong base, for example sodium hydride or sodium amide, and a $C_1$-$C_4$alkylhalide in an anhydrous inert solvent, for example DMF or THF, into compounds of formula I wherein $R_1$ is methyl or ethyl and $R_3$ is $C_1$-$C_4$alkyl.

1,2-Saturated compounds of formula I can be dehydrogenated in a manner known per se to form the corresponding 1,2-dehydro derivatives. For this purpose it is possible to use biological dehydrogenating methods, for example dehydrogenation using the microorganisms Corynebacterium Simplex or Septomyxa affinis or the enzyme systems thereof, or treatment with selenium dioxide in an organic solvent, for example tert-butyl alcohol Preferably, however, the dehydrogenation is carried out with 2,3-dichloro-5,6-dicyano-1,4-benzoquinone (optionally in the presence of bis(trimethylsilyl)-trifluoroacetamide, in which case an intermediate O-trimethlylsilylimidate is formed) or with benzeneseleninic acid anhydride over a period of several hours, for example from 6 to 24 hours, and optionally at room temperature or elevated temperature, for example at boiling temperature, in organic solvents, for example aromatic hydrocarbons, such as benzene or xylene, lower aliphatic alcohols, such as ethanol, propanol or tert-butyl alcohol, lower aliphatic ketones, such as acetone or 2-butanone, aliphatic esters, such as ethyl acetate, or cyclic ethers, such as dioxane or tetrahydrofuran.

The invention relates also to those forms of the process in which a compound obtainable as intermediate at any stage of the process is used as starting material and the remaining process steps are carried out, or the process is interrupted at any stage, or in which a starting material is formed under the reaction conditions or is used in the form of a derivative, for example a salt thereof.

The starting materials used in the processes of this invention are known or are obtainable by known methods (cf. G. H. Rasmusson et at., J. Med. Chem. 29, 2298–2315 (1986); J. Am. Chem. Soc. (JACS) 110, 3318 (1988)) and are preferably those which result in the compounds defined at the beginning as being especially valuable.

The pharmaceutical compositions of this invention comprising a compound of formula I can be used for the treatment of the above-mentioned indications, especially for the treatment of benign hypertrophy of the prostate. They comprise an effective amount of the active ingredient on its own or in admixture with inorganic or organic, solid or liquid, pharmaceutically acceptable carriers and, if desired, also with other pharmacologically or therapeutically valuable substances, and are suitable especially for enteral, for example oral or rectal, or parenteral, for example transdermal, administration or for topical application.

The present invention relates especially to pharmaceutical compositions comprising as active ingredient at least one compound of formula I according to the invention in the form of a sterile and/or isotonic aqueous solution or alternatively in admixture with at least one solid or semi-solid carrier.

The present invention relates also to medicaments, and especially to medicaments in unit dose forms, that comprise at least one of the compounds according to the invention on its own or in admixture with one or more carriers, especially those in solid form.

The invention relates especially to medicaments in the form of tablets (including lozenges, granules and pastilles), dragées, capsules, pills, ampoules, dry-filled vials or suppositories, comprising the above-defined active ingredient on its own or in admixture with one or more carriers.

The carriers for use in the pharmaceutical compositions (for example granules) for the preparation of tablets, dragées, capsules and pills are, for example, the following:

a) diluents, for example starch, sugars (such as lactose, glucose and saccharose), mannitol, sorbitol and silicic acid, b) binders, for example carboxymethylcellulose and other cellulose derivatives, alginic acid and salts thereof (such as sodium alginate), gelatin and polyvinylpyrrolidone, c) humectants, for example glycerol, d) disintegrators, for example agar-agar, calcium carbonate and sodium hydrogen carbonate, e) retardants for slowing the absorption of the active ingredient, for example paraffin, f) absorption accelerators, for example quaternary ammonium compounds, g) surface-active agents, for example cetyl alcohol and glycerol monostearate, h) adsorbents, for example kaolin and bentonite, i) flow-conditioners and lubricants, for example talc, calcium stearate, magnesium stearate and solid polyethylene glycols.

The tablets, dragées, capsules and pills comprising the above-mentioned pharmaceutical compositions according to the invention can be provided with the customary coatings and coverings with which, if desired, colourings or pigments may be mixed, for example for identification purposes. Those coatings may also be of a composition that allows the delayed release of the active ingredient; for those purposes there are suitable, for example, waxes and cellulose preparations, such as acetylcellulose phthalate or hydroxypropylmethylcellulose phthalate.

Those compositions may also be formulated in the form of microcapsules.

Suitable rectally administrable pharmaceutical compositions are, for example, suppositories that consist of a combination of the active ingredient and a suppository base. Suitable suppository bases are, for example, natural or synthetic triglycerides, paraffin hydrocarbons, polyethylene glycols or higher alkanols.

For parenteral administration there are especially suitable aqueous solutions of an active ingredient in water-soluble form, for example in the form of a water-soluble salt, or aqueous injection suspensions that contain viscosity-increasing substances, for example sodium carboxymethylcellulose, sorbitol and/or dextran, and, if desired, stabilisers. The active ingredient, optionally together with excipients, may also be in the form of a lyophilisate and can be made into a solution prior to parenteral administration by the addition of suitable solvents.

A composition for topical application may be in the form of an aqueous solution, a gel, an oily solution or suspension or a fat-containing or, especially, emulsified ointment. A composition in the form of an aqueous solution is obtained, for example, by dissolving the active ingredients according to the invention in an aqueous buffer solution of pH 4 to 6.5 and, if desired, adding a further active ingredient, for example an anti-inflammatory agent, and/or a polymeric binder, for example polyvinylpyrrolidone, and/or a preservative. The concentration of active ingredient is from approximately 0.1 to approximately 1.5 mg, preferably from 0.25 to 1.0 mg in 10 ml of solution or 10 g of gel.

An oily dosage form for topical application is obtained, for example, by suspending an active ingredient according to the invention in an oil, if desired with the addition of swelling agents, such as aluminium stearate, and/or surface-active substances (surfactants) having an HLB value of less than 10, such as fatty acid monoesters of polyols, for example glycerol monostearate, sorbitan monolaurate, sorbitan monostearate or sorbitan monooleate. A fat-containing ointment is obtained, for example, by suspending an active ingredient according to the invention or a salt thereof in a spreadable fatty base, if desired with the addition of a surfactant having an HLB value of less than 10. An emulsified ointment is obtained by trituration of an aqueous solution of the active ingredient according to the invention in a soft spreadable base with the addition of a surfactant having an HLB value of less than 10. All these forms for topical application may also contain preservatives. The concentration of the active ingredient is from approximately 0.1 to approximately 1.5 mg, preferably from 0.25 to 1.0 mg in approximately 10 g of base.

The pharmaceutical compositions according to the invention preferably comprise from approximately 0.1 to approximately 99.5 % by weight, especially from approximately 1 to approximately 90 % by weight, active ingredient.

The invention relates also to a method of treating the above-mentioned pathological conditions, the compounds according to the invention preferably being used in the form of pharmaceutical compositions. In such a method, a daily dose of from approximately 1 mg to approximately 100 mg will be administered to an individual of 70 kg body weight in the case of parenteral or enteral administration.

The above-mentioned pharmaceutical compositions and medicaments according to the invention are prepared by means of conventional preparation processes of the pharmaceutical industry that are known per se, for example by means of customary mixing, granulating, tabletting, confectioning, dissolving and lyophilising processes; if desired, the compositions and medicaments are prepared under aseptic conditions or an intermediate or a finished product is sterilised.

In the following Examples, which illustrate but do not limit the invention, temperatures are given in degrees Celsius. All melting points are uncorrected. The angle of rotation $[\alpha]_D$ is measured at a temperature of 20°.

EXAMPLE 1

(2-Cyanoethyl)-3-oxo-4-aza-5α-androstane-17β-carboxylate

At room temperature under an argon atmosphere, 1.2 ml of 1-chloro-1-dimethylamino-2-methylprop-1-ene in 6 ml of chloroform are added, with stirring, to a suspension of 638 mg (2 mmol) of 4-aza-3-oxo-5α-androstane-17β-carboxylic acid in 30 ml of chloroform (freshly filtered over basic aluminium oxide) and the mixture is stirred for a further two hours. The resulting clear solution, which comprises 3-oxo-4-aza-5α-androstane-17β-carboxylic acid chloride, is added dropwise, with stirring, at 4° to a solution of 1.2 ml of 3-hydroxypropionitrile in 6 ml of chloroform and the mixture is stirred for 2 hours at room temperature. The reaction mixture is diluted with 5 ml of ice-water and extracted twice with methylene chloride. The organic phases are washed with saturated sodium chloride solution, dried and concentrated by evaporation. Chromatography of the residue over 25 g of silica gel using a mixture of toluene/acetone (4:1) yields (2-cyanoethyl)-3-oxo-4-aza-5α-androstane-17β-carboxylate which, after crystallisation from methylene chloride/diisopropyl ether, melts at 233–235°, $[\alpha]_D = +55.8°$ (c=0.554 in chloroform).

EXAMPLE 2

N-(5-cyanopentyl)-3-oxo-4-aza-5α-androstane-17β-carboxamide 1.59 g of benzotriazol-1-yloxy-tris(dimethylamino)-phosphonium hexafluorophosphate (Castros reagent), 0.6 ml of methylmorpholine and 2.3 ml of 6-aminocapronitrile are added to a suspension of 957 mg (3 mmol) of 3-oxo-4-aza-5α-androstane-17β-carboxylic acid in 6.6 ml of dimethylformamide and the mixture is stirred for 2 hours at room temperature. The resulting solution is diluted with chloroform and washed in succession with sodium hydrogen carbonate solution, water and saturated sodium chloride solution. The organic phase is dried with sodium sulfate and concentrated to dryness under a water-jet vacuum. The residue is chromatographed over a column of silica gel using a mixture of toluene/methanol (97:3) as eluant, yielding N-(5-cyanopentyl)-3-oxo-4-aza-5α-androstane-17β-carboxamide, m.p. 213–215°, $[\alpha]_D = +41.0°$ (C=0.488 in chloroform) after crystallisation from methylene chloride/diisopropyl ether.

EXAMPLE 3

3-Cyano-2-methyl-2-propyl-3-oxo-4-aza-5α-androstane-17β-carboxylate

In a manner analogous to that described in Example 1, 3-oxo-4-aza-5α-androstane-17β-carboxylic acid chloride is reacted with 3-hydroxy-3-methylbutyronitrile in chloroform and processed further. Chromatography on silica gel with a mixture of toluene/methanol (98:2) yields 3-cyano-2-methyl-2-propyl-3-oxo-4-aza-5α-androstane-17β-carboxylate which, after crystallisation from methylene chloride/diisopropyl ether, melts at 225°–227°, $[\alpha]_D = +59.6°$ (c=0.534 in chloroform).

EXAMPLE 4

N-(4-cyanophenyl)-3-oxo-4-aza-5α-androstane-17β-carboxamide

In a manner analogous to that described in Example 1, the 3-oxo-4-aza-5α-androstane-17β-carboxylic acid chloride formed is reacted with 4-aminobenzonitrile in chloroform and processed further, yielding N-(4-cyanophenyl)-3-oxo-4-aza-5α-androstane-17β-carboxamide, m.p.>330°, $[\alpha]_D 32 + 120.8°$ (c=0.582 in chloroform/methanol (1:1)).

EXAMPLE 5

N-(2-cyano-2-propyl)-3-oxo-4-aza-5α-androstane-17β-carboxamide

Analogously to the process described in Example 1, 3-oxo-4-aza-5α-androstane-17β-carboxylic acid chloride is reacted with 2-amino-2-methylpropionitrile in chloroform and processed further, yielding N-(2-cyano-2-propyl)-3-oxo-4-aza-5α-androstane- 17β-carboxamide, m.p. 304°–306°, $[\alpha]_D = +83.4°$ (c=0.519 in chloroform/methanol (1:1)),

EXAMPLE 6

2-Cyanoethyl-3-oxo-4-aza-5α-androst-1-ene-17β-carboxylate 372 mg (1 mmol) of (2-cyanoethyl)-3-oxo-4-aza-5α-androstane-17β-carboxylate, 1.4 ml of N,O-bis(trimethylsilyl)trifluoroacetamide and 238 mg of 2,3-dichloro-5,6-dicyano-1,4benzoquinone are suspended in 8 ml of absolute dioxane and under argon first stirred for 4 hours at 25° and then heated at reflux for 16 hours. The dark-red solution formed during the reaction is then concentrated to half. For working up, the residue is diluted with 30 ml of methylene chloride and washed in succession with 1% sodium bisulfite solution and saturated aqueous sodium chloride solution. The aqueous portions are re-extracted with methylene chloride and the combined organic portions are dried over sodium sulfate and concentrated by evaporation. The resulting crude product is chromatographed over silica gel (toluene/acetone=9:1) and the uniform fractions are subsequently crystallised from methylene chloride/diisopropyl ether, yielding pure 2-cyanoethyl-3-oxo-4-aza-5α-androst-1-ene-17βcarboxylate having a melting point of 259°–261°, $[\alpha]_D = +2.9°$ (c=0.481 in chloroform).

EXAMPLE 7

3-Cyano-2-methyl-2-propyl-3-oxo-4-aza-5α-androst-1-ene-17β-carboxylate

Analogously to Example 6, 3-cyano-2-methyl-2-propyl-3-oxo-4-aza-5α-androstane-17β- carboxylate is reacted with N,O-bis(trimethylsilyl)trifluoroacetamide and 2,3-dicyano-5,6-dichlorobenzoquinone in dioxane and processed further, yielding 3-cyano-2-methyl-2-propyl-3-oxo-4-aza-5α-androst-1-ene-17β-carboxylate, m.p. 211–213°, $[\alpha]_D = +6.5°$ (c=0.428 in chloroform).

EXAMPLE 8

N-(5-cyanopentyl)-3-oxo-4-aza-5α-androst-1-ene-17β-carboxamide

In a manner analogous to Example 6, N-(5-cyanopentyl)-3-oxo-4-aza-5α-androstane-17β-carboxamide is reacted with N,O-bis(trimethylsilyl)trifluoroacetamide and 2,3-dichloro5,6-dicyano-1,4-benzoquinone and processed further. The crude product is chromatographed on silica gel with a mixture of methylene chloride/acetone (4:1), yielding N-(5-cyanopentyl)-3-oxo-4-aza-5α-androst-1-ene-17β-carboxamide having a melting point of 188°–190°, $[\alpha]_D = -8.8°$ (c=0.433 in chloroform) after crystallisation from methylene chloride/diisopropyl ether.

EXAMPLE 9

N-(4-cyanophenyl)-3-oxo-4-aza-5α-androst-1-ene-17β-carboxamide

In a manner analogous to Example 6, N-(4-cyanophenyl)-4-aza-3-oxo-5α-androstane-17β-carboxamide is reacted with N,O-bis(trimethylsilyl)trifluoroacetamide and 2,3-dichloro-5,6-dicyano-1,4-benzoquinone and processed further. The crude product is chromatographed on silica gel with a mixture of methylene chloride/methanol (9:1), yielding chromatographically uniform N-(4-cyanophenyl)-3-oxo-4-aza-5α-androst-1-ene-17β-carboxamide having a melting point of >330°, $[\alpha]_D = +90.3°$ (c=0.404 in chloroform/methanol (2:1)) after crystallisation from methylene chloride/diisopropyl ether.

EXAMPLE 10

N-(2-cyano-2-propyl)-3-oxo-4-aza-5α-androst-1-ene-17β-carboxamide

In a manner analogous to Example 6, N-(2-cyano-2-propyl)-3-oxo-4-aza-3-oxo-5α-androstane-17β-carboxamide is reactor with N,O-bis(trimethylsilyl)trifluoroacetamide and 2,3-dichloro-5,6-dicyano-1,4-benzoquinone and processed further. The crude product is chromatographed over silica gel with a mixture of methylene chloride/acetone (4:1), yielding N-(2-cyano-2-propyl )-3 -oxo-4-aza-5α-androst-1-ene-17β-carboxamide which, after being recrystallised once from methylene chloride/diisopropyl ether, melts at 289°–291°, $[\alpha]_D = +14.3°$ (C=0.384 in chloroform).

EXAMPLE 11

N-(2-cyano-2-propyl)-3-oxo-4-aza-5α-androst-1-ene-17β-carboxamide 951 mg (3 mmol) of 3-oxo-4-aza-5α-androst-1-ene-17βcarboxylic acid (J. Am. Chem. Soc. 110, 3318 (1988)) are suspended in 50 ml of chloroform, and 4.8 ml of thionyl chloride in 21 ml of chloroform are added at from 10° to 15° C. within a period of 5 minutes. The resulting solution is stirred for one hour. The reaction mixture is then concentrated to dryness under a high vacuum. The residue, which comprises 3-oxo-4-aza-5α-androst-1-ene-17β-carboxylic acid chloride, is dissolved in 60 ml of chloroform, and at 25°, with stirring, 0.2 ml of triethylamine and 1.95 ml of 2-amino-2-methylpropionitrile in 18 ml of chloroform are added dropwise in succession thereto and the mixture is stirred at room temperature for 3 hours. The reaction mixture is diluted with 60 ml of ice-water and extracted with methylene chloride. The organic phase is washed with saturated sodium chloride solution, dried and concentrated under a water-jet vacuum. The residue is chromatographed on a column of silica gel using a mixture of methylene chloride/acetone (9:1) as eluant, yielding N-(2-cyano-2-propyl)-3-oxo-4-aza-5α-androst-1-ene-17β-carboxamide which, after crystallisation from methylene chloride/diisopropyl ether, melts at 291°–295°.

EXAMPLE 12

N-(2-cyano-2-propyl)-4-methyl-3-oxo-4-aza-5α-androstane-17β-carboxamide

Analogously to the process described in Example 11, N-(2-cyano-2-propyl)-4-methyl-3-oxo-4-aza-5α-androstane-17β-carboxamide is prepared from 4-methyl-3-oxo-4-aza-5α-androstane-17β-carboxylic acid (J. Med. Chem. 27, 1690 (1984)); after crystallisation from methylene chloride/diisopropyl ether the title compound melts at 233°–235° C.; $[\alpha]_D = +49.3°$ (c=0.475 in chloroform)

EXAMPLE 13

N-(2-cyano-2-propyl)4-methyl-3-oxo-4-aza-5α-androst-1-ene-17β-carboxamide

Analogously to the process described in Example 11, from 4-methyl-3-oxo-4-aza-5α-androst-1-ene-17β-carboxylic acid (J. Med. Chem. 29, 2298 (1986)) there is obtained N(-2-cyano-2-propyl)-4-methyl-3-oxo-4-aza-5α-androst-1-ene-17β-carboxamide which, alter recrystallisation from methylene chloride/diisopropyl ether, melts at 231°–235°; $[\alpha]_D = +3.8°$ (c=0.44 in chloroform).

EXAMPLE 14

N-(3-cyano-3-pentyl)-3-oxo-4-aza-5α-androst-1-ene-17β-carboxamide

In a manner analogous to that described in Example 11, the 3-oxo-4-aza-5α-androst-1-ene-17β-carboxylic acid chloride formed is reacted with 2-amino-2-ethyl-butyronitrile in chloroform and processed further, yielding N-(3-cyano-3-pentyl)-3-oxo-4-aza-5α-androst-1-ene-17βcarboxamide, m.p. 280°–288°, $[\alpha]_D = +13.7°$ (c=0.467 in chloroform).

EXAMPLE 15

N-(2-Cyano-2-butyl)-3-oxo-4-aza-5α-androst-1-ene-17β-carboxamide

In a manner analogous to that described in Example 11, the 3-oxo-4-aza-5α-androst-1-ene-17β-carboxylic acid chloride formed is reacted with 2-amino-2-methyl-butyronitrile in chloroform and processed further, yielding N-(2-cyano-2-butyl)-3-oxo-4-aza-5α-androst-1-ene-17β-carboxamide, m.p. 262°–265°.

EXAMPLE 16

N-(1-cyano-1-cyclopropyl)-3-oxo-4-aza-5α-androst-1-ene-17β-carboxamide

In a manner analogous to that described in Example 11, the dried 3-oxo-4-aza-5α-androst-1-ene-17β-carboxylic acid chloride formed (1 mmol) is dissolved in 12 ml of chloroform, and at 25° C., with stirring, reacted dropwise with 0.3 ml of triethylamine and a suspension of 472 mg (4 mmol) of 1-amino-1-cyclopropanecarbonitrile hydrochloride (J. Org. Chem. 55, 4281 (1990)) and 0.73 ml of N-ethyldiisopropylamine and processed further, yielding N-(1-cyano-1-cyclopropyl)-3-oxo-4-aza-5α-androst-1-ene-17β-carboxamide; m.p. 312°–315°.

EXAMPLE 17

N-(1-cyano-3-cyclopentyl)-3-oxo-4-aza-5α-androst-1-ene-17β-carboxamide

In a manner analogous to that described in Example 11, the 3-oxo-4-aza-5α-androst-1-ene-17β-carboxylic acid chloride formed is reacted with 1-amino-1-cyclopentanecarbonitrile in chloroform and processed further, yielding N-(1-cyano-1-cyclopentyl)-3-oxo-5α-androst-1-ene-17β-carboxamide, m.p. 262°–269°, $[\alpha]_D = +18.8°$ (c=0.54 in chloroform).

EXAMPLE 18

N-(1-cyano-1-cyclohexyl)-3-oxo-4-aza-5α-androst-1-ene-17β-carboxamide

In a manner analogous to that described in Example 11, the 3-oxo-4-aza-5α-androst-1-ene-17β-carboxylic acid chloride formed is reacted with 1-amino-1-cyclohexanecarbonitrile in chloroform and processed further, yielding N-(1-cyano-1-cyclohexyl)-3-oxo-5α-androst-1-ene-17β-carboxamide. m.p. 292°–300°, $[\alpha]_D = +18.7°$ (c=0.486 in chloroform).

EXAMPLE 19

N-(2-cyanophenyl)-3-oxo-4-aza-5α-androst-1-ene-17β-carboxamide

In a manner analogous to that described in Example I 1,3-oxo-4-aza-5α-androst-1-ene-17β-carboxylic acid chloride is reacted with 2-aminobenzonitrile in chloroform and processed further, yielding N-(2-cyanophenyl)-3-oxo-4-aza-5α-androst-1-ene-17β-carboxamide, m.p. 296°–304°.

EXAMPLE 20

N-(3-cyanophenyl)-3-oxo-4-aza-5α-androstane-17β-carboxamide

Analogously to the process described in Example 1, 4-aza-3-oxo-5α-androstane-17β-carboxylic acid chloride is reacted with 3-aminobenzonitrile in tetrahydrofuran and processed further, yielding N-(3-cyanophenyl)-3-oxo-4-aza-5αandrostane-17β-carboxamide, m.p. 299°–301°.

EXAMPLE 21

N-(2-cyanophenyl)-3-oxo-4-aza-5α-androstane-17β-carboxamide

Analogously to the process described in Example 1, 4-aza-3-oxo-5α-androstane-17βcarboxylic acid chloride is reacted with 3-aminobenzonitrile in chloroform and processed further, yielding N-(2-cyanophenyl)-3-oxo-4-aza-5α-androstane-17β-carboxamide, m.p. 298°–306°.

EXAMPLE 22

N-(3-cyanophenyl)-3-oxo-4-aza-5α-androst-1-ene-17β-carboxamide

In a manner analogous to that described in Example 6, N-(3-cyanophenyl)-3-oxo-4-aza-5α-androstane-17β-carboxamide is reacted with N,O-bis(trimethylsilyl)trifluoroacetamide and 2,3-dichloro-5,6-dicyano-1,4-benzoquinone and processed further. The crude product is chromatographed on silica gel with a mixture of methylene chloride/acetone (4:1), yielding N-(3-cyanophenyl)-3-oxo-4-aza-5α-androst-1-ene-17β-carboxamide which, after crystallisation from methylene chloride/diisopropyl ether, melts at 318°–321°.

EXAMPLE 23

N,N-(methyl)(2-cyano-2-propyl)-4-methyl-3-oxo-4-aza-5α-androst-1-ene-17βcarboxamide 0.4 ml of methyl iodide and 80 mg of sodium hydride dispersion are added to a solution of 144 mg (0.3 retool) of N-(2-cyano-2-propyl)-3-oxo-4-aza-5α-androst-1-ene-17β-carboxamide in 3.0 ml of absolute tetrahydrofuran and the mixture is stirred at room temperature under an argon atmosphere for 5 hours. For working up, the reaction mixture is poured into 5 ml of ice-water and 1 ml of acetic acid and extracted twice with methylene chloride. The organic phases are washed with saturated sodium chloride solution, dried and concentrated by evaporation. The residue is chromatographed over silica gel with a mixture of methylene chloride/acetone (95:5), yielding N,N-(methyl)(2-cyano-2-propyl)-4-methyl-3-oxo-4-aza-5α-androst-1-ene-17β-carboxamide which, after crystallisation from methylene chloride/diisopropyl ether, melts at 218°–221°; $[\alpha]_D = +25.8°$ (c=0.485 in chloroform).

EXAMPLE 24

Tablets, comprising 10 mg of active ingredient, for example N-(2-cyano-2-propyl)-3-oxo-4aza-5α-androst-1-ene-17β-carboxamide or a different compound of Examples 1-23, are prepared as follows:

| Composition for 5 000 tablets | |
|---|---|
| active ingredient, micronised | 50.0 g |
| saccharose | 79.0 g |
| gum arabic | 4.75 g |
| sorbitol | 3.75 g |
| talc | 2.5 g |
| magnesium stearate | 4.9 g |
| mineral oil | 0.1 g |
| carboxymethylcellulose (sodium salt) | 5.0 g |

Preparation

The active ingredient is mixed with the powdered saccharose and the gum arabic, sieved and granulated using an approximately 35% aqueous sorbitol solution. The granules are forced through a sieve, dried, sieved again and homogeneously mixed with the remaining excipients (talc, magnesium stearate, mineral oil and the sodium salt of carboxymethylcellulose). The mixture is compressed in customary manner to give 10 mg tablets.

EXAMPLE 25

Tablets, comprising 1 mg of active ingredient, for example N-(2-cyano-2-propyl)-3-oxo-4-aza-5α-androst-1-ene-17β-carboxamide or a different compound of Examples 1-23, are prepared as follows:

| Composition for 50 000 tablets | |
|---|---|
| active ingredient, micronised | 50.0 g |
| saccharose | 79.0 g |
| gum arabic | 4.75 g |
| sorbitol | 3.75 g |
| talc | 2.5 g |
| magnesium stearate | 4.9 g |
| mineral oil | 0.1 g |
| carboxymethylcellulose (sodium salt) | 5.0 g |

Preparation

The active ingredient is mixed with the powdered saccharose and the gum arabic, sieved and granulated using an approximately 35% aqueous sorbitol solution. The granules are forced through a sieve, dried, sieved again and homogeneously mixed with the remaining excipients (talc, magnesium stearate, mineral oil and the sodium salt of carboxymethylcellulose). The mixture is compressed in customary manner to give 1 mg tablets.

What is claimed is:

1. A compound of the formula

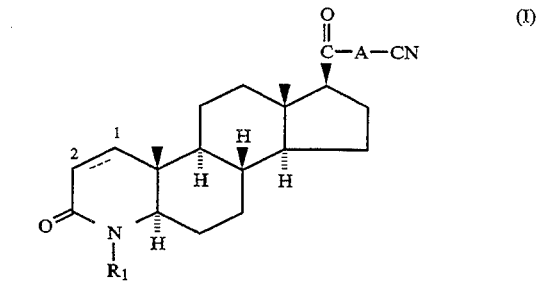

wherein carbon atoms 1 and 2 are linked by a single bond or a double bond; $R_1$ is hydrogen, methyl or ethyl; A is a group of the formula —N(—$R_2$)—X— or —O—X—, wherein $R_2$ is hydrogen or $C_1$–$C_4$alkyl and X is $C_1$–$C_{12}$alkylene.

2. The compound of claim 1 wherein $R_1$ is hydrogen or methyl; $R_2$ is hydrogen; and X is a straight or branched $C_1$–$C_6$ alkylene.

3. The compound of claim 1 wherein carbon atoms 1 and 2 are linked by a double bond; A is —N(—$R_2$)—X—; $R_2$ is hydrogen; and X is $C_1$–$C_4$alkylene.

4. N-(2-cyano-2-propyl)-3-oxo-4-aza-5α-androst-1-ene-17β-carboxamide according to claim 1.

5. N-(2-cyano-2-propyl)-4-methyl-3-oxo-4-aza-5α-androstane-17β-carboxamide according to claim 1.

6. A pharmaceutical composition comprising an effective 5α-reductase inhibiting amount of a compound according to claim 1 and a pharmaceutically acceptable carrier therefor.

* * * * *